United States Patent
Carbone (10) Patent No.: US 9,622,789 B2
(45) Date of Patent: Apr. 18, 2017

(54) SPINAL FIXATION DEVICE AND METHOD

(75) Inventor: John Carbone, Lutherville, MD (US)

(73) Assignee: K2M, Inc., Leesburg, VA (US)

( * ) Notice: Subject to any disclaimer, the term of this patent is extended or adjusted under 35 U.S.C. 154(b) by 261 days.

(21) Appl. No.: 12/812,829

(22) PCT Filed: Jan. 12, 2009

(86) PCT No.: PCT/US2009/030721
§ 371 (c)(1),
(2), (4) Date: Aug. 18, 2010

(87) PCT Pub. No.: WO2009/091689
PCT Pub. Date: Jul. 23, 2009

(65) Prior Publication Data
US 2010/0305616 A1    Dec. 2, 2010

Related U.S. Application Data

(60) Provisional application No. 61/011,014, filed on Jan. 14, 2008.

(51) Int. Cl.
*A61B 17/70* (2006.01)

(52) U.S. Cl.
CPC ...... *A61B 17/7044* (2013.01); *A61B 17/7032* (2013.01); *A61B 17/7035* (2013.01)

(58) Field of Classification Search
CPC ........ A61B 17/8625; A61B 2017/8655; A61B 17/844; A61B 17/7056; A61B 17/7007; A61B 17/7011; A61B 17/7044; A61B 17/7058; A61B 17/7064; A61B 17/707; A61B 17/7071; A61B 17/7073

USPC ................. 606/246–279, 300–321
See application file for complete search history.

(56) References Cited

U.S. PATENT DOCUMENTS

| | | | | |
|---|---|---|---|---|
| 5,269,784 A * | 12/1993 | Mast | ............................. | 606/288 |
| 5,306,275 A * | 4/1994 | Bryan | ........................... | 606/914 |
| 5,415,659 A * | 5/1995 | Lee et al. | ...................... | 606/276 |
| 5,507,747 A * | 4/1996 | Yuan et al. | .................... | 606/276 |
| 5,584,832 A * | 12/1996 | Schlapfer | ........... | A61B 17/7056 606/276 |
| 5,611,800 A | 3/1997 | Davis et al. | | |
| 5,667,506 A | 9/1997 | Sutterlin | | |
| 5,810,816 A * | 9/1998 | Roussouly et al. | ........... | 606/246 |

(Continued)

FOREIGN PATENT DOCUMENTS

| | | |
|---|---|---|
| FR | 2 813 782 | 3/2002 |
| JP | H 08336548 | 12/1996 |

(Continued)

OTHER PUBLICATIONS

Australian Patent Examination Report for Application No. 200905575 dated Feb. 15, 2013 (3 pages).

(Continued)

*Primary Examiner* — Lynnsy Summitt
(74) *Attorney, Agent, or Firm* — Carter, DeLuca, Farrell & Schmidt, LLP (57) ABSTRACT

A spinal fixation device includes a fastener affixable to a vertebral body and an attachment member. The attachment member is adapted for receiving the fastener and engaging a portion of the vertebral body. The fastener includes a shank and a collet. The collet includes a channel for receiving a spinal rod and a locking member.

12 Claims, 7 Drawing Sheets

(56) References Cited

U.S. PATENT DOCUMENTS

| | | | |
|---|---|---|---|
| 6,030,162 A * | 2/2000 | Huebner | 411/413 |
| 6,261,288 B1 * | 7/2001 | Jackson | A61B 17/7052 |
| | | | 606/250 |
| 6,322,562 B1 * | 11/2001 | Wolter | 606/62 |
| 6,488,681 B2 | 12/2002 | Martin et al. | |
| 6,749,361 B2 | 6/2004 | Hermann et al. | |
| 6,974,478 B2 | 12/2005 | Reiley et al. | |
| 7,338,490 B2 * | 3/2008 | Ogilvie et al. | 606/276 |
| 7,635,365 B2 * | 12/2009 | Ellis et al. | 606/71 |
| 7,645,294 B2 * | 1/2010 | Kalfas et al. | 606/250 |
| 2004/0106925 A1 * | 6/2004 | Culbert | 606/73 |
| 2004/0111091 A1 * | 6/2004 | Ogilvie et al. | 606/73 |
| 2004/0220570 A1 | 11/2004 | Frigg | |
| 2004/0260296 A1 * | 12/2004 | Kaiser | A61F 2/0811 |
| | | | 623/13.11 |
| 2006/0116676 A1 | 6/2006 | Gradel et al. | |
| 2007/0213732 A1 * | 9/2007 | Khanna et al. | 606/73 |
| 2008/0255619 A1 * | 10/2008 | Schneiderman et al. | 606/276 |

FOREIGN PATENT DOCUMENTS

| | | |
|---|---|---|
| JP | 2002233532 | 8/2002 |
| WO | WO 94/00062 A1 | 1/1994 |
| WO | WO 94/21186 | 9/1994 |
| WO | WO 00/64365 | 11/2000 |
| WO | WO 2004/064654 A1 | 8/2004 |
| WO | WO 2005/032386 | 4/2005 |
| WO | WO 2008/060930 A2 | 5/2008 |

OTHER PUBLICATIONS

Japanese Office Action dated Apr. 9, 2013 in counterpart Japanese Patent Application No. 2010-542399.
European Examination Report dated Sep. 30, 2013 in European Application No. 09 702 226.
European Search Report dated Nov. 20, 2012 in copending European Patent Appln. No. 09 702 226.
Australian Examination Report dated Oct. 10, 2016, issued in Australian Application No. 2014203776.

* cited by examiner

SPINAL FIXATION DEVICE AND METHOD

CROSS-REFERENCE TO RELATED APPLICATIONS

This application is a national stage application of International Application Number PCT/US2009/030721, filed on Jan. 12, 20009, which claims priority to, and the benefit of, U.S. Provisional Patent Application Ser. No. 61/011,014, filed on Jan. 14, 2008, the entire contents of each of these prior applications are hereby incorporated by reference.

BACKGROUND

1. Technical Field

The present disclosure relates to devices and methods for use in orthopedic spine surgery. In particular, the present disclosure relates to a device and methods for coupling a spinal rod to a patient's vertebral body.

2. Background of Related Art

The human spine is comprised of thirty-three vertebrae at birth and twenty-four as a mature adult. The vertebra includes the vertebral body and posterior elements, including the spinous process, transverse processes, facet joints, laminae, and pedicles. The vertebral body consists of a cortical shell surrounding a cancellous center. Between each pair of vertebrae is an intervertebral disc, which maintains the space between adjacent vertebrae and acts as a cushion under compressive, bending and rotational loads and motions. A healthy intervertebral disc consists mostly of water in the nucleus pulposus, which is the center portion of the disc. The water content gives the nucleus a spongy quality and allows it to absorb spinal stresses.

There are many diseases, such as spondylolisthesis and scoliosis, and injuries that affect the vertebral and intervertebral discs. Excessive pressure or injuries to a disc can result in injury to the annulus, which is the outer ring that holds the disc together. Generally, the annulus is the first portion of the disc to be injured. These injuries are typically in the form of small tears that heal by forming scar tissue. The scar tissue is not as strong as normal annulus tissue and weakens over time. This can lead to damage of the nucleus pulposus. When damaged, the nucleus will begin to lose its water content and will dry up. As the nucleus loses its water content, it collapses, allowing the vertebrae above and below the disc space to move closer to one another. This results in a narrowing of the disc space between the vertebrae and an imbalance in the spinal column. As a result, the discs will lose their ability to act as shock absorbers or cushions. The increased load and wear due to the biomechanical imbalance of the spine initiates a cascading deleterious effect.

When a disc or vertebra is damaged due to disease or injury, standard practice is to remove part or all of the intervertebral disc, insert a natural or artificial disc spacer along with bone graft, and construct an internal bracing structure to hold the affected vertebrae in place in an attempt to achieve a spinal fusion. Typically, the structure is created by inserting screws through the pedicle and cortical shell of the vertebra and into the cancellous center of the vertebral body. Then, a rod is rigidly attached to the screws securing the vertebrae in place.

Osteoporosis, a disease that causes low bone mass and deterioration of bone tissue, is an additional challenge when trying to create an internal structure to stabilize the spine. When osteoporosis affects the spine, the lack of quality bone compromises the screw's ability to gain adequate purchase. Since osteoporosis affects the cancellous, more porous, bone before affecting the denser cortical bone, greater fixation is achievable by taking advantage of posterior elements that are mainly cortical bone rather than the vertebral body alone. For patients suffering from scoliosis, an abnormal curvature of the spine, posterior spinal elements also present a strong point of fixation from which manual correction of the spine may be applied and then internally braced.

SUMMARY

Disclosed herein is a spinal fixation device and a method for its implantation in the spine. The spinal fixation device includes a fastener affixable to a vertebra, such as by screwing into the vertebral pedicle and an attachment member having a body portion and an arm portion extending therefrom, the body portion including an opening for receiving the fastener, the arm portion adapted to engage at least a portion of the vertebral body. The fastener may include a threaded portion and may further include a head movable relative to the threaded portion. The threaded portion may include more than one pitch, e.g., threads at a proximal end of the threaded portion may have one pitch and threads at a distal end may have another pitch. The opening may include a locking mechanism to secure the fastener therein. The locking mechanism may include a rimmed edge along the opening, the rimmed edge engageable with at least one thread on the fastener.

The spinal fixation device may be attached to a vertebra by providing a hook having a through hole and a curved protrusion and a bone anchor, positioning the through hole over a pedicle of a vertebral body, engaging the curved protrusion with a portion of the vertebra and inserting the bone anchor through the through hole and into the pedicle. An opening in the pedicle may be made prior to inserting the bone anchor into the pedicle. Once the spinal fixation device is installed in the vertebral body, a spinal rod or plate may be attached to each bone anchor on at least one side of the spine.

BRIEF DESCRIPTION OF THE DRAWINGS

Embodiments of the present disclosure are described herein with reference to the accompanying drawings, wherein.

DETAILED DESCRIPTION

Particular embodiments of the present disclosure will be described herein with reference to the accompanying drawings. In the following description, well known functions or constructions are not described in detail to avoid obscuring the present disclosure in unnecessary detail. As shown in the drawings and as described throughout the following descriptions, and as is traditional when referring to relative positioning on an object, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for purposes of this application, the term "medial" indicates a direction toward a side of the body of the patient, i.e., away from the middle of the body of the patient. The term "posterior" indicates a direction toward the patient's back, and the term "anterior" indicates a direction toward the patient's front.

A spinal fixation device 10 will now be described with reference to FIGS. 1-4. The spinal fixation device 10 includes an intralaminar hook 100 and a pedicle screw 200.

Figure 1:
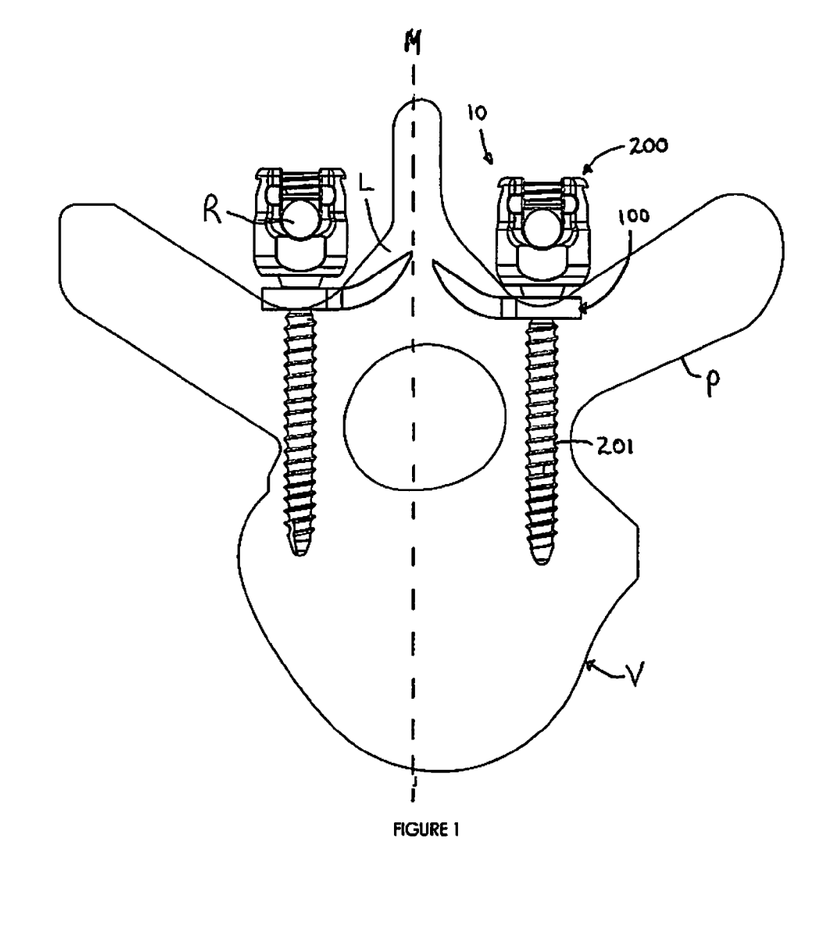
FIG. 1 is a transverse plane view of a spinal fixation device including a pedicle screw and an intralaminar hook placed within a vertebra.
Figure 2:
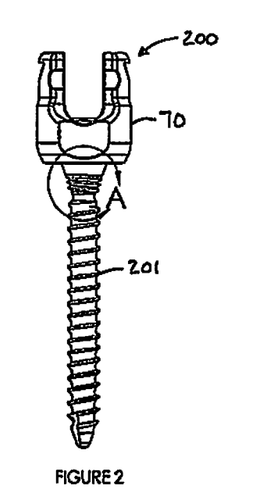
FIG. 2 is a front view of the pedicle screw of FIG. 1.
Figure 2A:
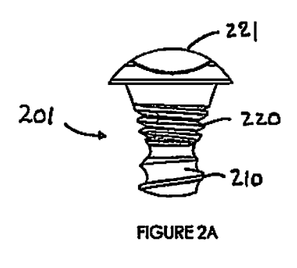
FIG. 2A is an enlarged view of detail A of the pedicle screw of FIG. 2
Figure 3:
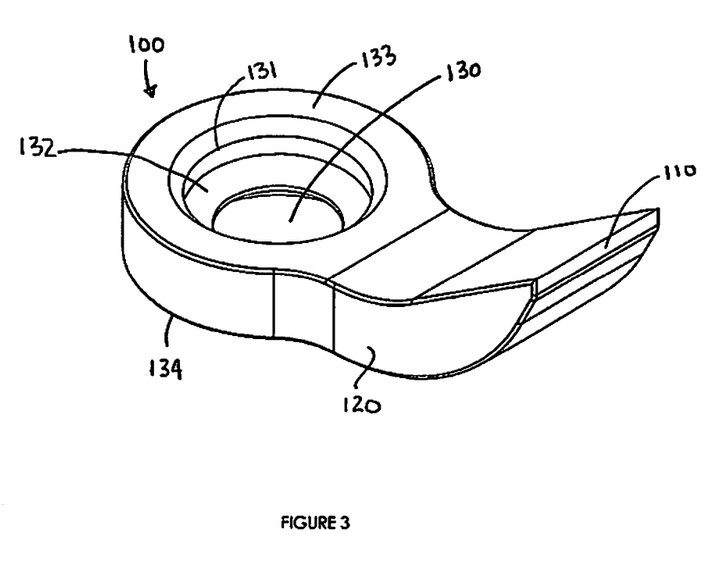
FIG. 3 is an isometric view of the intralaminar hook of FIG. 1.
Figure 4:
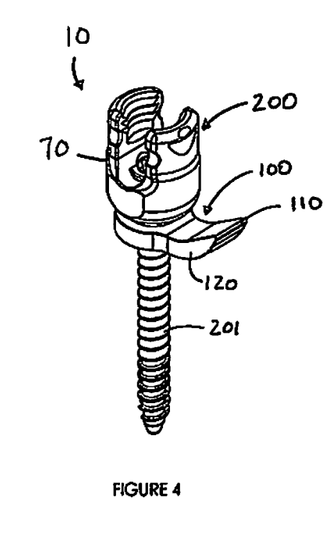
FIG. 4 is an isometric view of the spinal fixation device of FIG. 1.

The intralaminar hook 100, shown best in FIG. 3, includes a bone anchor through hole 130 of sufficient size to receive a shank 201 of a pedicle screw 200, shown in FIGS. 2-2A, and to provide an adequate seating surface for a head 221 of the pedicle screw 200. The laminar hook further includes a curved protrusion 120. As shown in FIG. 1, the laminar hook 100 is of a sufficient length to approach midline M of the vertebra V. However, in other embodiments, the dimensions and orientation of the laminar hook 100 may differ.

An exemplary pedicle screw 200 including a shank 201 and a collet 70, shown in FIG. 2, may be of a rigid, unitary design or may be polyaxial. Examples of polyaxial screws are found in U.S. Pat. Nos. 5,733,286; 5,683,392; and 6,451,021, Published U.S. Patent Application 20080027432, and International Patent Applications Serial Nos. PCT/US08/80682 and PCT/US08/80668, the entire contents of which are incorporated herein by reference. In the exemplary polyaxial screw shown in FIG. 2, the collet 70 of the pedicle screw 200 is configured and dimensioned to receive head 221 of the shank 201 such that the collet 70 and the head 221 are rotatable and pivotable in relation to each other, thereby allowing the shank 201 to be repositioned in a plurality of orientations relative to the collet 70.

The shank 201 optionally may have a dual pitch thread whereby proximal threads 220 have a different pitch than distal threads 210, as shown in FIG. 2A. The distal threads 210 are adapted for aggressive purchase in cancellous bone. The proximal threads 220 have a finer pitch thread. The proximal threads 220 may be removably or permanently fixed to an annular sidewall 131 of the bone anchor through hole 130 upon insertion of the pedicle screw 200 therethrough. Such a locking mechanism may also be included on laminar hook 300 and pedicle hook 400, described below. A screw locking mechanism of this type is disclosed in U.S. Pat. No. 6,322,562, the entire contents of which are incorporated by reference.

The bone anchor through hole 130 has an annular sidewall 131 extending downward from a top surface 133. A lip 132 is located in the bone anchor through hole 130 in proximity to a bottom surface 134. The lip 132 is configured for engaging the proximal threads 220 of the shank 201 such that rotating the shank 201 causes the proximal threads 220 to engage the lip 132 such that the pedicle screw 200 is secured in the bone anchor through hole 130 and resists backing out of the bone anchor through hole 130. In this optional configuration, the material of the intralaminar hook 100 (i.e. commercially pure titanium) is softer than that of the pedicle screw 200 (i.e. Ti-6AL-4V alloy) to allow proximal threads 220 of shank 201 to engage the lip 132 as the shank 201 is inserted into the bone anchor through hole 130 and resists backing out of the bone anchor through hole 130. The proximal threads 220 engage the lip 132 when the pedicle screw 200 is in various angular orientations with respect to the axis of the bone anchor through hole 130.

It will be understood, however, that the pedicle screw 200 may be secured to bone without the use of such a locking mechanism since the interaction of the pedicle screw 200 and one of intralaminar hook 100, laminar hook 300, and pedicle hook 400 would provide an adequate fixation point.

Installation of the spinal fixation device 10 is achieved by positioning the bone anchor through hole 130 over a pedicle P of a vertebra V and embedding the curved protrusion 120 of the intralaminar hook 100 within a lamina L of the vertebra V. A tapered end 110 of the curved protrusion 120 may ease insertion of the curved protrusion into the lamina L. Once the curved protrusion 120 has been affixed to the lamina L with the through hole 130 positioned over the pedicle, the screw shank 201 is then driven through the bone anchor through hole 130 and into the pedicle P, thereby fixing the intralaminar hook 100 between the pedicle screw 200 and the pedicle P, as shown in FIG. 1. Once the spinal fixation device 10 is installed in the vertebra V, a spinal rod R or plate (not shown) is affixable to the pedicle screw 200.

Figure 5:
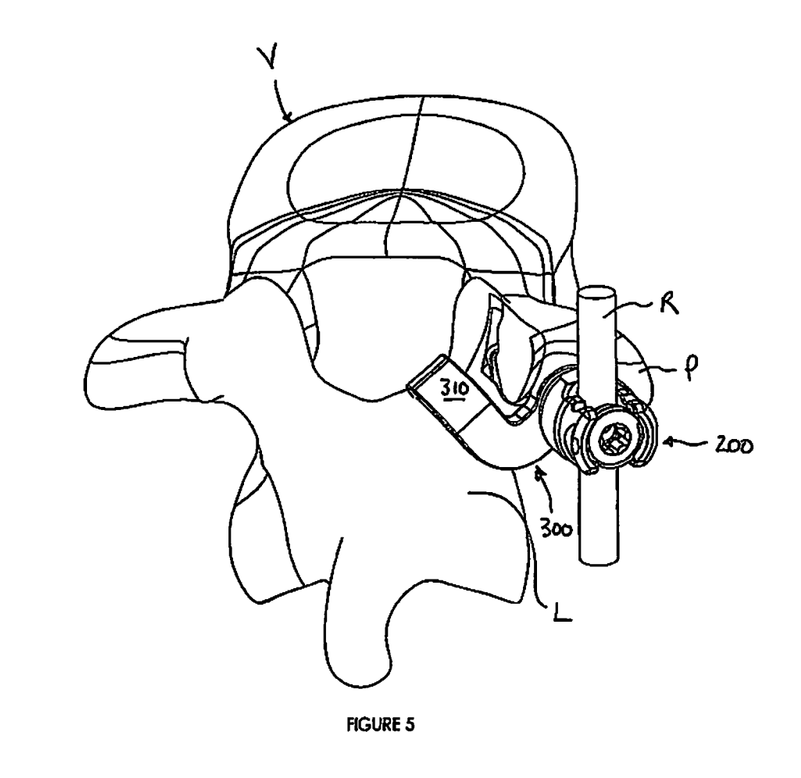
FIG. 5 is an isometric view of a spinal fixation device including a pedicle screw and a laminar hook affixed to a vertebra.
Figure 6:
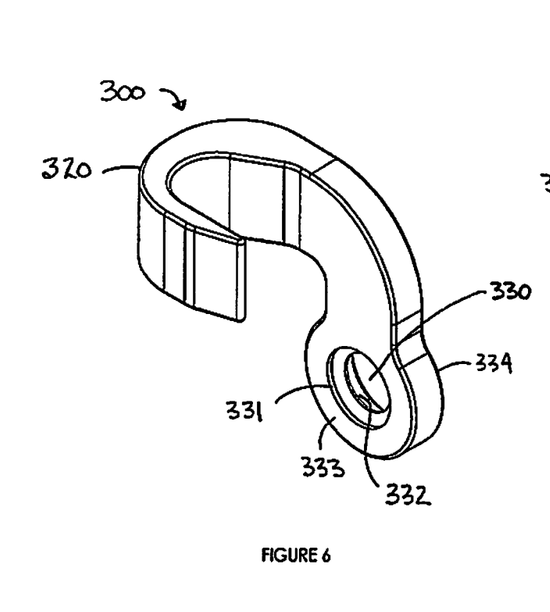
FIG. 6 is an isometric view of the laminar hook of FIG. 5.
Figure 7:
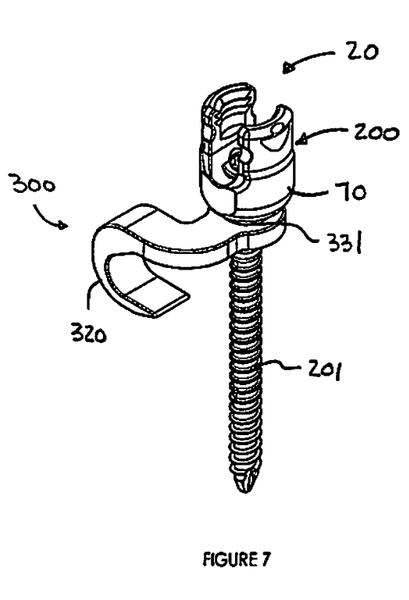
FIG. 7 is an isometric view of the spinal fixation device of FIG. 5.

A spinal fixation device 20 is shown in FIGS. 5-7, including a laminar hook 300 and the pedicle screw construct 200. The laminar hook 300 includes a curved protrusion 310 to hook around and onto the lamina L, and a bone anchor through hole 330 to receive the pedicle screw 200, as shown in FIG. 5. In FIG. 5 the hook is shown hooked onto the superior edge surface of the lamina, but it is contemplated that the hook could be configured to hook onto the inferior edge surface of the lamina.

Using a posterior exposure, the pedicle P may be prepared by making a pilot hole in the pedicle P using known instruments and techniques. Next, the laminar hook 300 is attached to a surface of the lamina L. The through hole 330 is then placed over the pilot hole. The pedicle screw 200 is then inserted through the through hole 330 and into the pilot hole and into the pedicle P. Optional proximal threads 220 may lock with an optional annular sidewall 331 extending downward from a top surface 333 and lip 332 located in the through hole 330 in proximity to a bottom surface 334 and configured to engage the proximal threads 220 of the shank 201 (FIG. 6), as discussed above with reference to intralaminar hook 100. When the pedicle screw 200 is fully seated, the spinal fixation device 20 has two areas of fixation, one at the shank 201 positioned in the pedicle P and vertebral body V and the other where the spinal fixation device 20 is secured to the lamina L. A spinal rod R or a plate (not shown) may then be attached to the pedicle screw 200.

Figure 8:
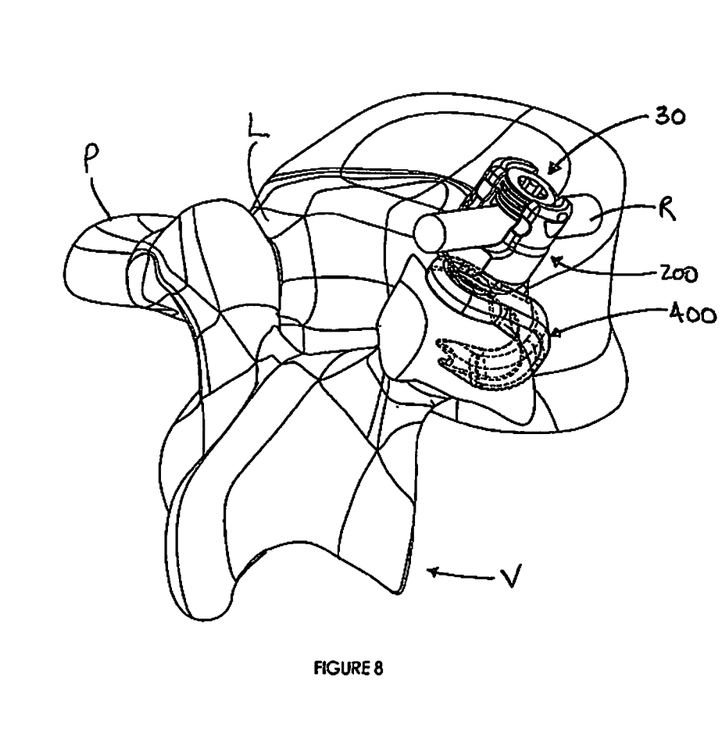
FIG. 8 is an isometric view of a spinal fixation device including a pedicle screw and a pedicle hook.
Figure 9:
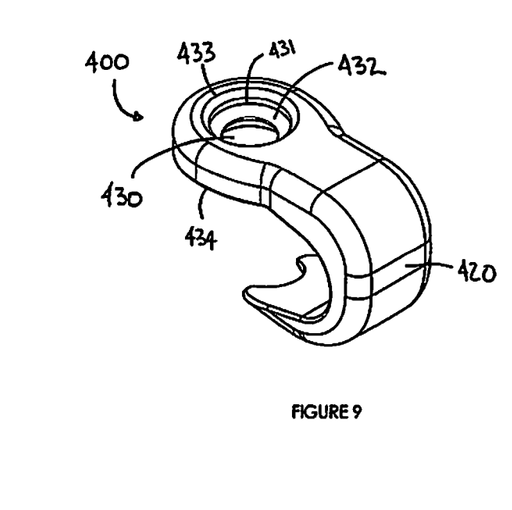
FIG. 9 is an isometric view of the pedicle hook of FIG. 8.
Figure 10:
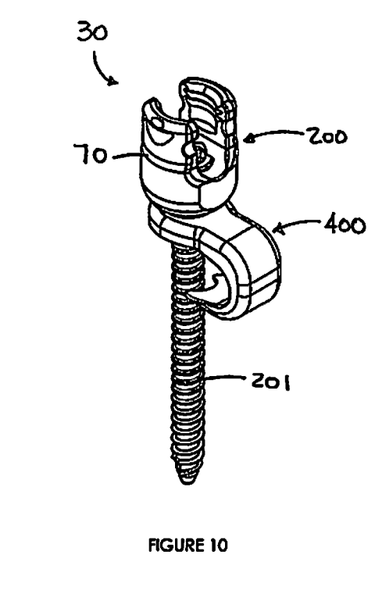
FIG. 10 is an isometric view of the spinal fixation device of FIG. 8.

Another embodiment of a spinal fixation device 30 is shown in FIGS. 8-10. As seen in FIG. 8, the spinal fixation device 30 includes a pedicle hook 400 including a curved protrusion 420 that is anchorable to the pedicle and the pedicle screw construct 200 receivable within a bone anchor through hole 430 of the pedicle hook. Optional proximal threads 220 are removably or permanently fixable to an annular sidewall 431 extending downward from a top surface 433 and optional lip 432 located in the through hole 430 in proximity to a bottom surface 434 and configured to engage the proximal threads 220 of the shank 201, as previously described with respect to the intralaminar hook 100.

Installation of the spinal fixation device 30 is achieved by making a pilot hole using known instruments and techniques in the pedicle P for receipt of the pedicle screw 200 and positioning the through hole 430 of the pedicle hook 400 over the pilot hole and positioning the pedicle hook 400 about a surface of the pedicle P. In FIG. 8 the pedicle hook is shown extends around the pedicle in the region of the inferior vertebral notch to provide enhanced stability and fixation of the pedicle screw. Alternatively, it is contemplated that the pedicle hook could be configured and dimensioned engage the area of the pedicle toward the superior vertebral notch. As yet a further alternative, the hook could be configured and dimensioned to penetrate a portion of the pedicle. Next, the shank 201 is inserted through the through hole 430 and into the pedicle P. When the shank 201 is fully seated, the screw and fixation device 30 has two areas of fixation, one at the shank 201 positioned in the pedicle P and vertebral body V and the other where the spinal fixation device 30 is secured to the pedicle P. A spinal rod R or a plate (not shown) is then attached to the pedicle screw 200.

Alternative embodiments of the method and device disclosed herein are contemplated and will be apparent to those skilled in the art from the present disclosure. For example, it will be understood that where the disclosure refers to a pedicle screw, any suitable bone anchor may be used. Additionally, the dimensions, shapes, and orientations of the curved protrusions 120, 320, and 420 may be modified to better fit a patient's unique anatomical characteristics while remaining within the spirit of the disclosure. In this regard, while the illustrations show the attachment device in the context of lumbar anatomy, it will be understood that the device could be configured and dimensioned for use in the cervical spine, thoracic spine, sacrum or other applications where supplemental fixation of a fastener in bone. In addition, while the preferred locking mechanism for the screw to attachment device interface is as described, it is contemplated that the attachment portion of the attachment device need not constitute a through hole, but could incompletely surround the screw shaft or other configuration provided the screw and attachment member suitably engage each other. In this regard, other optional locking mechanisms to secure the screw to the attachment member also are contemplated, such as a compression ring, threads in the attachment member through hole to engage threads on the fastener, a floating or movable threaded ring in the through hole to engage threads on the fastener shaft, or a portion of the attachment member to engage a notch or opening in the screw shaft, etc. The threads on the fastener to engage the attachment member may be on the fastener shaft or the fastener head.

What is claimed is:

1. A spinal fixation device comprising:
a fastener including a head and a shank, the shank having a threaded portion, the shank configured for penetration into at least a first portion of a vertebral body, the threaded portion of the shank includes a first thread portion at a proximal portion of the shank which has a first thread pitch and a second thread portion at a distal portion of the shank which has a second pitch different from the first pitch; and
an attachment member having a body portion and an arm portion extending therefrom and configured to engage at least a second portion of the vertebral body, the body portion including an opening configured and dimensioned to receive at least a portion of the fastener therethrough when the arm portion engages the second portion of the vertebral body and the shank of the fastener penetrates into the first portion of the vertebral body, the opening including a locking mechanism to secure the fastener to the attachment member, the locking mechanism having a rimmed edge extending from a sidewall of the opening and in proximity to a bottom surface of the body portion, the rimmed edge engaging at least one thread on the shank.

2. The spinal fixation device of claim 1, wherein the arm portion is configured and dimensioned to penetrate bone.

3. The spinal fixation device of claim 2, wherein the arm portion is configured and dimensioned to penetrate a lamina of the vertebral body.

4. The spinal fixation device of claim 2, wherein the arm portion is configured and dimensioned to penetrate a pedicle of the vertebral body.

5. The spinal fixation device of claim 1, further including a locking device attachable to a portion of the fastener for securing a spinal rod to the fastener.

6. The spinal fixation device of claim 1, wherein the arm portion is configured and dimensioned to hook to a portion of the vertebral body adjacent to the fastener.

7. The spinal fixation device of claim 6, wherein the arm portion is configured and dimensioned to hook to a lamina of the vertebral body.

8. The spinal fixation device of claim 6, wherein the arm portion is configured and dimensioned to hook to a pedicle of the vertebral body.

9. The spinal fixation device of claim 1, wherein the shank is laterally spaced from the arm portion.

10. A spinal fixation device comprising:
a fastener including a head and a shank, the shank having a threaded portion, the shank configured for penetration into at least a first portion of a vertebral body;
an attachment member having a body portion and an arm portion extending therefrom and configured to engage at least a second portion of the vertebral body, the body portion including an opening configured and dimensioned to receive at least a portion of the fastener therethrough when the arm portion engages the second portion of the vertebral body and the shank of the fastener penetrates into the first portion of the vertebral body, the opening including a locking mechanism to secure the fastener to the attachment member, the locking mechanism having a rimmed edge extending from a sidewall of the opening and in proximity to a bottom surface of the body portion, the rimmed edge engaging at least one thread on the shank, wherein the opening is an unthreaded through hole and the rimmed edge is an annular lip extending from the sidewall of the through hole; and
a locking device attachable to a portion of the fastener for securing a spinal rod to the fastener.

11. The spinal fixation device of claim 10, wherein the arm portion is configured and dimensioned to penetrate bone.

12. The spinal fixation device of claim 10, wherein the arm portion is configured and dimensioned to hook to a portion of the vertebral body adjacent to the fastener.

* * * * *